United States Patent [19]

Price, Jr.

[11] Patent Number: 5,334,213
[45] Date of Patent: Aug. 2, 1994

[54] CORNEAL PRESS

[76] Inventor: Francis W. Price, Jr., 5511 Sunset La., Indianapolis, Ind. 46208

[21] Appl. No.: 137,908

[22] Filed: Oct. 15, 1993

[51] Int. Cl.$^5$ .......................... A61F 9/00; A61B 17/32
[52] U.S. Cl. ..................................... 606/166; 606/184
[58] Field of Search ................ 606/166, 167, 184, 107

[56] References Cited

U.S. PATENT DOCUMENTS

| | | | |
|---|---|---|---|
| 3,058,471 | 10/1962 | Shope | 606/166 |
| 4,190,050 | 2/1980 | Bailey | 606/166 |
| 4,236,519 | 12/1980 | La Russa et al. | 606/184 |
| 4,718,420 | 1/1988 | Lemp | 606/166 |
| 5,011,498 | 4/1991 | Krumeich et al. | 606/166 |
| 5,084,059 | 1/1992 | Metzger | 606/166 |
| 5,092,874 | 3/1992 | Rogers | 606/166 |

*Primary Examiner*—Ralph Lewis
*Attorney, Agent, or Firm*—Woodard, Emhardt, Naughton Moriarty & McNett

[57] ABSTRACT

A corneal press is disclosed for accurately trephining corneal tissue. The disclosed press includes a base support member, a modular cutting block, two guide posts, a collet mount, a threaded drive mechanism, and a set of modular collets. The base includes means for securely holding the cutting block in position for holding a corneal specimen to be cut about a defined axis. The guide posts are attached to the base in offset parallel alignment relative to the defined axis. The collet mount is mounted onto the guide posts and is slidable relative thereto toward and away from a corneal specimen positioned on the cutting block mounted onto the base. The threaded drive mechanically links the collet mount to the base such that the operation of the threaded drive causes the collet mount to move along said guide posts toward or away from a specimen positioned on the base. Each of a set of modular collets are mountable to the collet mount and are configured to securely hold a trephine of a specifically defined diameter in centered alignment about the defined axis. When so positioned for a cutting operation, the operation of the threaded drive causes the trephine to move along the defined axis and to precisely cut a specimen of corneal tissue positioned on the base about said axis. An alignment sight hole, which extends through collet mount in alignment with said defined axis and which is co-aligned with a sight hole extending a collet mounted therein, allows for the visual alignment of the cut to be made and also provides a means for directing illumination onto the cutting area during a cutting procedure.

4 Claims, 5 Drawing Sheets

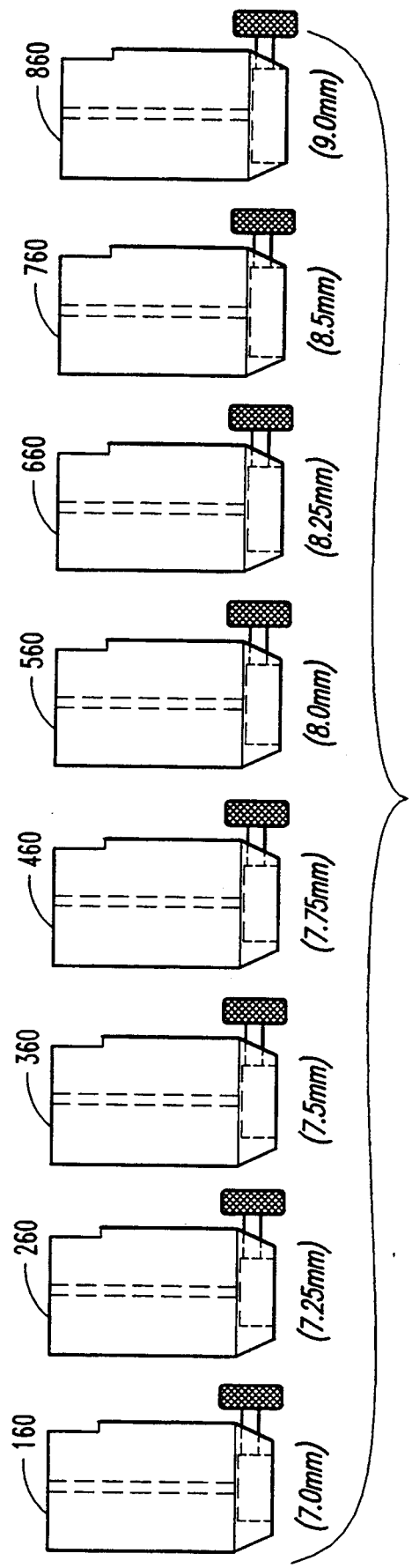
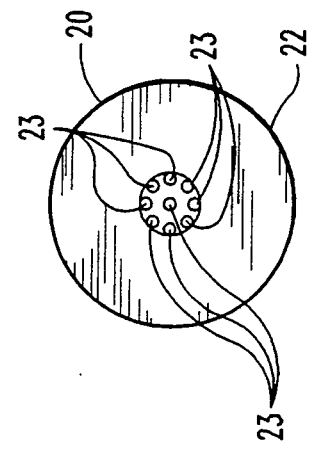
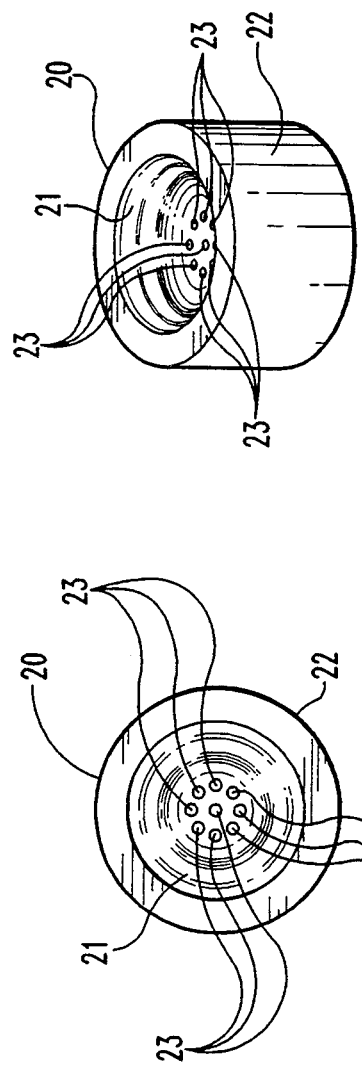
Fig. 5
Fig. 6a
Fig. 6b
Fig. 6c

1

CORNEAL PRESS

BACKGROUND OF THE INVENTION

Corneal transplants, by which healthy corneal tissue of a donor is transplanted to replace diseased corneal tissue of a receiving patient, have become a common surgical procedure in the field of ophthalmology in recent years. In such a procedure, the donor tissue must be precisely cut to match the size and shape of the corneal tissue that has been removed from the patient who is to receive the transplant. In the past, the cutting of the donor tissue has commonly been done with the use of hand-held trephines. Hand cutting of the donor tissue, though, fails to provide enough precision for reliably accurate transplantation.

Mechanically aided corneal press devices have also been used, such as that described in U.S. Pat. No. 5,092,874 to Rogers, and U.S. Pat. No. 4,718,420 to Lemp. While more accurate than hand-held devices, mechanically aided presses have generally not provided the desired precise accuracy that is required over a range of cutting diameters and for long-term repeated use at a reasonable cost. These mechanisms must not only operate precisely through numerous repetitions of movement, they must also be able to do so after repeated autoclaving since each individual cutting procedure must be performed under sterile conditions. Mechanisms that have been devised to maintain accuracy through repeated use and after repeated autoclaving have been complicated and expensive to manufacture.

Accordingly, there is a need for an improved corneal press that precisely cuts corneal tissue over a range of diameters, and does so reliably for many repeated cuts and numerous corresponding autoclaving treatments over a long period of time. Additionally, there is a need for such a device which is not complicated as to its structure and is relatively inexpensive to manufacture.

SUMMARY OF THE INVENTION

The present invention provides a new corneal press which makes precise cuts of corneal tissue over a range of diameters. The device of the present invention, which incorporates a threaded drive mechanism for precisely controlled advancement of a trephine against the tissue to be cut and utilizes a set of modular collets which are each individually machined to accommodate a trephine of a particular size, is easy to use and is designed to maintain its precision for many repeated uses over a long period of time.

As will be described in more detail in relation to the preferred embodiment, a corneal press according the present invention generally includes a base, a modular cutting block mountable therein, two guide posts, a collet mount, a threaded drive mechanism, and a set of modular collets. The base includes means for securely holding the cutting block in position for holding a corneal specimen to be cut about a defined axis. The guide posts are attached to the base in offset parallel alignment relative to the defined axis. The collet mount is mounted onto the guide posts and is slidable therealong toward and away from a corneal specimen positioned on the cutting block mounted onto the base. The threaded drive mechanically links the collet mount to the base such that the operation of the threaded drive causes the collet mount to move along said guide posts toward or away from a specimen positioned on the base.

There is also provided a set of modular collets which are each mountable to the collet mount and are individually configured to securely hold a trephine of a specifically defined diameter in centered alignment about the defined axis when the collet has been mounted onto said collet mount. When so positioned for a cutting operation, with a collet mounted to the collet mount and holding a trephine of a predefined diameter, the operation of the threaded drive causes the trephine to move along the defined axis and to precisely cut a specimen of corneal tissue positioned on the base about said axis. The cutting operation is precisely repeatable for a wide variety of cutting diameters and over a long period for many repeated uses.

To enhance the assured accuracy of the cut to be made, the corneal press described herein also incorporates an alignment sighting feature by which the alignment of a trephine about the defined cutting axis can be visually verified, and which is also useful for directing light onto the cutting area. An alignment sight hole, which extends through collet mount in alignment with said defined axis and which is co-aligned with a sight hole extending through a collet when properly mounted therein, allows for the visual alignment of the cut to be made and also provides a means for directing illumination onto the cutting area during a cutting procedure.

BRIEF DESCRIPTION OF THE DRAWINGS

FIG. 5 is a side elevational view of a set of collets for use with the corneal press of FIGS. 1-3, with each of said collets configured to hold a trephine of a particularly defined size.

FIGS. 6a–c are views of a modular cutting block 20 for use in corneal press 100 of FIGS. 1-3. FIG. 6a is a top plan view, FIG. 6b is a perspective view, and FIG. 6c is a bottom plan view of cutting block 20.

DESCRIPTION OF THE PREFERRED EMBODIMENT

Figure 1:
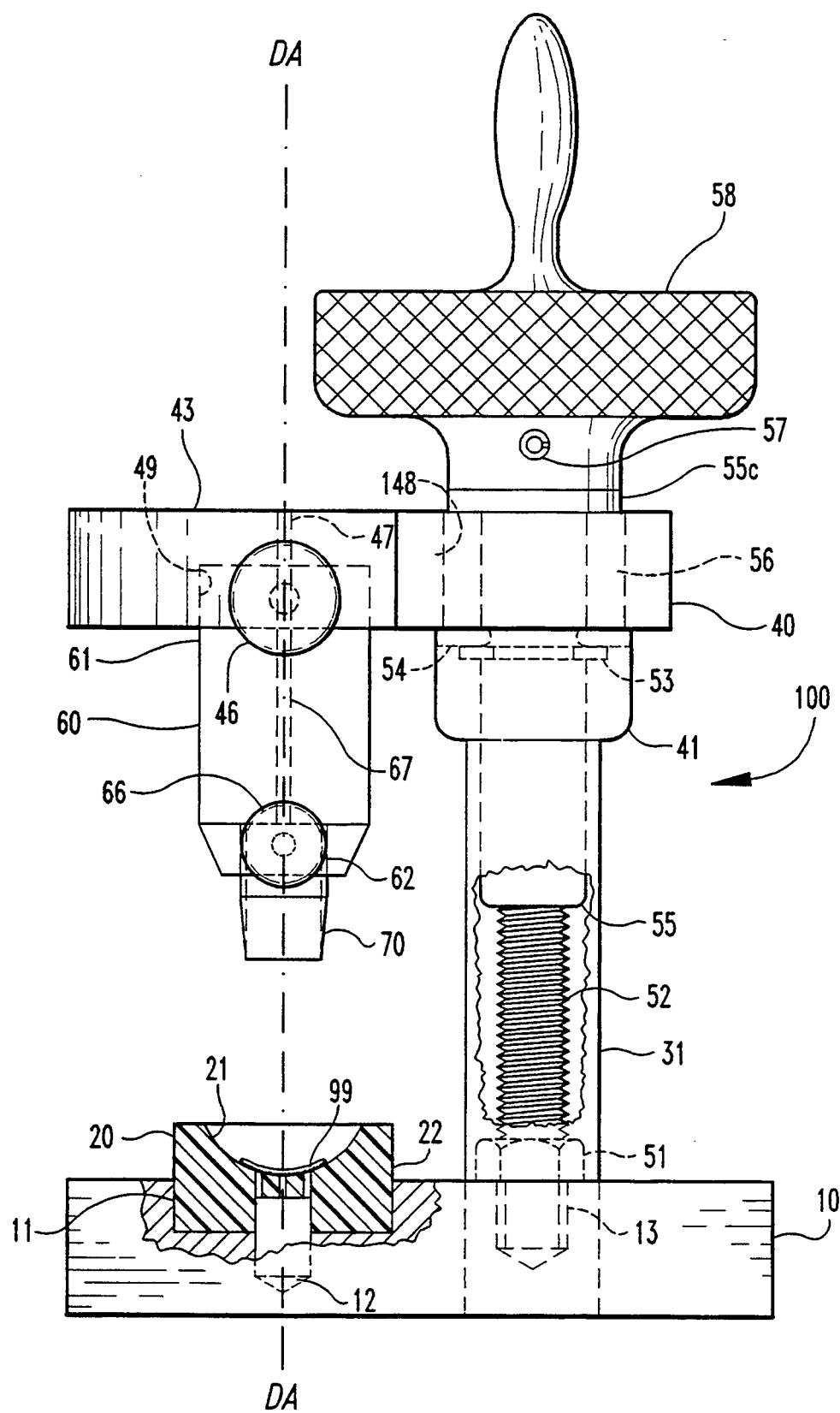
FIG. 1 is a partially sectioned, side elevational view of a corneal press according to the present invention.

For the purposes of promoting an understanding of tile principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
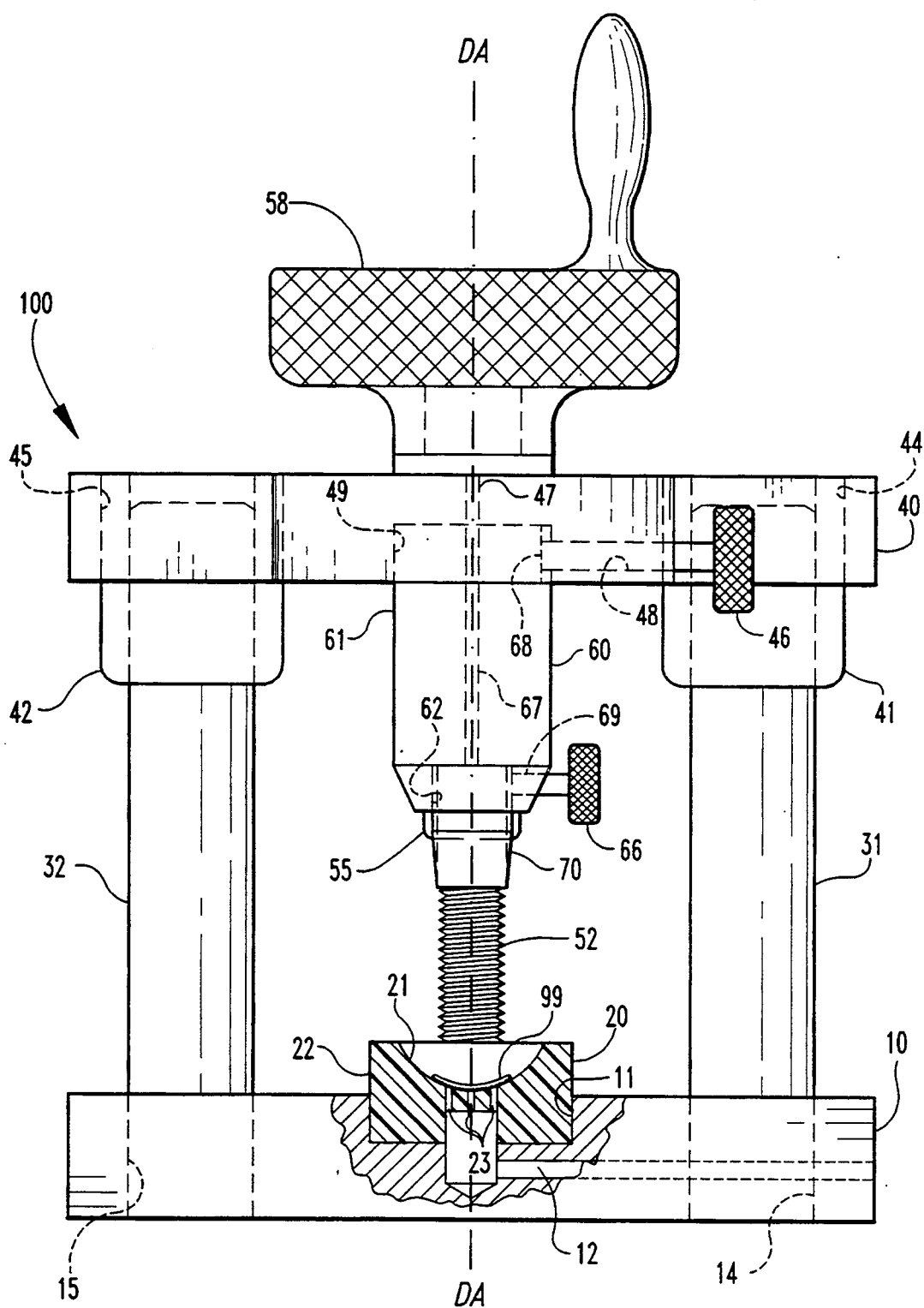
FIG. 2 is a partially sectioned, front elevational view of the corneal press of FIG. 1.
Figure 3:
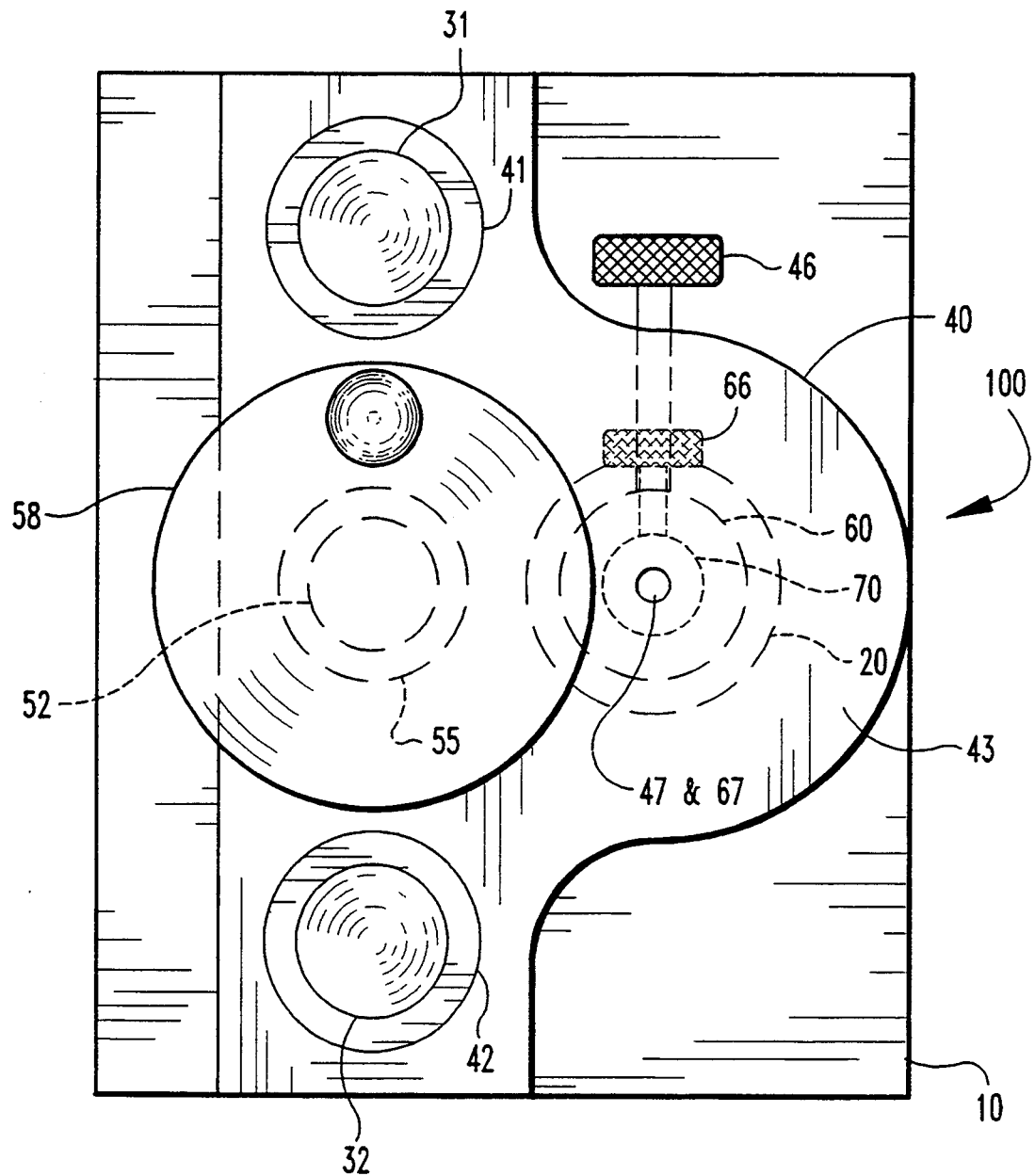
FIG. 3 is a top plan view of the corneal press of FIGS. 1 and 2.

Turning now to the drawings, FIGS. 1-3 show various views of a corneal press 100 according to the present invention. Corneal press 100 generally includes a base support member 10, modular cutting block 20, guide posts 31 and 32, collet mount 40, threaded drive mechanism 50, collet 60, and trephine 70. Modular cutting block 20, mounted to base 10 holds a corneal specimen 99 to be cut about a defined axis DA. Guide posts 31 and 32 are attached to base 10 in offset parallel alignment relative to defined axis DA. Collet mount 40, which is made of stainless steel, is mounted onto guide posts 31 and 32 and is slidable relative thereto toward and away from corneal specimen 99 positioned on base 10. Collet 60, which is also made of stainless steel, is mounted to collet mount 40 and securely holds trephine 70 in centered alignment about defined axis DA.

Threaded drive mechanism 50 mechanically links collet mount 40 to base 10, and operates to cause the movement of collet mount 40 along guide posts 31 and 32 toward or away from specimen 99. When corneal press 100 is thus positioned for a cutting operation, as shown in FIGS. 1 and 2, with collet 60 mounted to collet mount 40 and holding trephine 70 of a predetermined diameter, the operation of threaded drive mechanism 50 causes trephine 70 to move along defined axis DA to precisely cut specimen 99 into a shape of the desired diameter. This cutting operation is precisely repeatable for a wide variety of cutting diameters and over a long period for many repeated uses.

Turning now specifically to some of the particular features of corneal press 100, base 10 includes recess 11 which is sized to snugly receive modular cutting block 20. Cutting block 20 has a concave corneal tissue support surface 21 which conformingly receives corneal tissue specimen 99 to be cut by trephine 70. Outer surface 22 of cutting block 20 is circular in circumference and sized to snugly fit within recess 11 in base support member 10. Cutting block 20 further defines holes 23 therethrough which connect corneal tissue support surface 21 with suction passageway 12 in base support member 10. By drawing a vacuum in suction passageway 12, corneal tissue 99 can thus be stably positioned on corneal tissue support surface 21 for the cutting procedure, thereby preventing the slipping of corneal tissue 99 out of position which would adversely affect the accuracy of the cut to be made.

Cylindrical guide posts 31 and 32 are made of stainless steel and are fixedly mounted into correspondingly cylindrical holes 14 and 15 respectively in base 10. Base 10 is also made of stainless steel. Stainless steel sleeves 41 and 42 are fixedly mounted into holes 44 and 45 in collet mount 40, and are slidably mounted onto posts 31 and 32 respectively.

Collet 60 has an outer circumferential surface 61 which is receivable by recess 49, located within laterally extending portion 43 of collet mount 40, and is securely held therein by thumb screw 46. Thumb screw 46 screws into threaded hole 48 in collet mount 40 and against key 68 on collet 60 to secure the mounting of collet 60 onto collet mount 40. Trephine 70, likewise, has an outer circumferential surface which fits into recess 62 in collet 60, and is securely held therein by thumb screw 66. Thumb screw 66 screws into threaded hole 69 in collet 60 and against trephine 70 to secure the mounting of trephine 70 onto collet 60.

Collet mount 40 and collet 60 also define alignment holes 47 and 67, respectively, which pass therethrough in alignment with defined axis DA. Alignment holes 47 and 67 may be used to confirm alignment of the cut to be made by directly viewing corneal tissue 99 through holes 47 and 67 along defined axis DA. By looking through alignment holes 47 and 67, one can simply verify that collet 60 has been properly mounted onto collet mount 40, and has not been inadvertently mounted in a "cocked" position that would cause an improper cut to be made. Also, applying a light source above hole 47, alignment holes 47 and 67 may also be used to direct light onto specimen 99 positioned on cutting block 20, and to thereby provide illumination for the cutting procedure.

Figure 4:
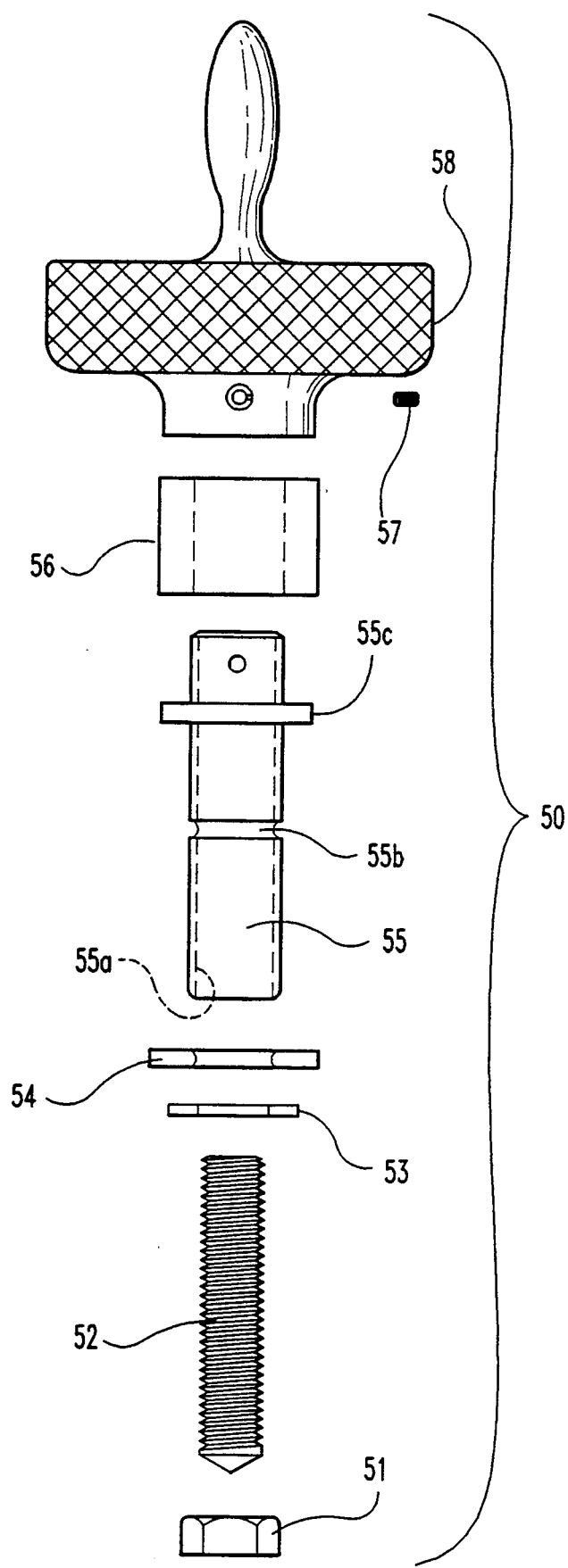
FIG. 4 is an exploded view of threaded drive mechanism 50 of FIGS. 1-3.

As shown in FIG. 4, threaded drive mechanism 50 includes nut 51, threaded bolt 52, jam nut 53, c-clip retaining ring 54, threaded sleeve 55, bushing 56, set screw 57, and handle 58, which are each made of stainless steel, except for bushing 56 which is made of brass. Bolt 52 is threaded into threaded recess 13 of base 10, and is held in place by nut 51 which is threaded about bolt 52 and against base 10. Threaded sleeve 55 has an internal threaded portion 55a which correspondingly matches the external thread on bolt 52, and also includes retaining groove 55b and retaining flange 55c. Bushing 56 is fixedly mounted within hole 148 in collet mount 40 while allowing the free rotation of sleeve 55 therewithin. Jam nut 53, which fits over sleeve 55, retaining ring 54, which fits onto groove 55b in sleeve, and flange 55c, which set atop bushing 56 and collet mount 40, serve to maintain threaded sleeve 55 in a longitudinally fixed, yet freely rotatable, position relative to collet mount 40. Set screw 57 attaches handle 58 to the upper portion of sleeve 55, which allows threaded drive mechanism 50 to be easily operated by the rotating of handle 58.

The operation of threaded drive mechanism 50 to provide the controlled advancement of trephine 70 against a specimen 99 of corneal tissue positioned on cutting block 20 will now be described. In this regard, it is to be appreciated that the turning of handle 58 rotates threaded sleeve 55 about threaded bolt 52, which causes threaded sleeve 55 to threadedly advance therealong. In that jam nut 53, retaining ring 54, and flange 55c attach threaded drive mechanism 50 to collet mount 40, collet mount 40 is also advanced along guide posts 31 and 32 by the rotating of handle 58. In this way, collet mount 40 can be moved along guide posts 31 and 32 to and away from cutting block 20.

By providing for the controlled advancement of trephine 70 against the corneal tissue to be cut, threaded drive mechanism 50 ensures that a precise and accurate cut is made. No lateral forces are applied which might cause an uneven cut to be made, and because the rate of advancement can be determined by selecting the rate of rotation of handle 58, the speed at which trephine 70 is moved to cut a specimen can be precisely controlled as well.

The present invention contemplates the use of a full set of collets which hold trephines over a range of expected diameter cuts, typically between 7.0 mm. and 9.0 mm. in diameter. Accordingly, FIG. 5 shows an example of a set of collets 600 which are for use in the operation of corneal press of FIGS. 1-3. Each collet in said set 600 is configured to hold a trephine of a particularly defined size and, collectively, the collets in collet set 600 hold trephines over a range of expected diameter cuts. Collet set 600, in particular, includes collets 160, 260, 360, 460, 560, 660, 760 and 860 for holding trephines of 7.0 mm., 7.25 mm., 7.5 mm., 7.75 mm., 8.0 mm., 8.25 mm., 8.5 mm., and 9.0 mm., respectively. It is contemplated that various combinations of the above sizes, or alternative sets of collets sizes for trephines of differently scaled dimensions would be useful as well, and the use of such alternate sizes or combinations would not adversely affect the beneficial usefulness of the present invention as described and claimed herein.

FIGS. 6a-c show various views of modular cutting block 20 on which a corneal specimen is placed for cutting by corneal press 100. In these figures, holes 23 are seen to be formed in a pattern in the central portion of concave surface area 21. The use of multiple holes in a pattern such as is shown in these drawings is helpful for providing a generally even amount of suction around the area of placement of a corneal tissue specimen, and is also helpful for the placement of orientation markings onto the tissue to aid in the positioning of the tissue during implantation.

Cutting block 20 is intended for one-time use, and is typically made of a suitable biocompatible material, such as silicone. It has also been found that harder materials work very well in conjunction with the operation of press 100, as the added hardness has the effect of enhancing the accuracy of the cut that results from the controlled advancement of trephine 70 against corneal tissue 99, as described above. An acetal resin, sold by E. I. DuPont de Nemours & Co. under the trademark of DELRIN, has been found to be one such suitable material.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. Corneal press apparatus for trephining corneal tissue, said press comprising:
   a) a modular cutting block for holding a specimen of corneal tissue in a concave position;
   b) a base support member, said base support member including means for securely holding said modular cutting block in position wherein said cutting block holds said specimen of corneal tissue in position centered about a defined axis;
   c) two guide posts attached to said base and rising therefrom, said guide posts being positioned in offset parallel alignment relative to said defined axis;
   d) a collet mount, said collet mount being slidably mounted onto said guide posts, said collet mount including collet-mounting means for receiving and securely holding a collet in centered alignment about said defined axis;
   e) a threaded drive mechanism mechanically linking said collet mount to said base support member such that the operation of said threaded drive causes said collet mount to slide along said guide posts; and
   f) a collet, said collet being holdably receivable by said collet-mounting means, said collet including trephine-mounting means for receiving and securely holding a trephine in centered alignment about said defined axis;
   whereby the operation of said threaded drive, with said collet being received and securely held by said collet-mounting means, and said received collet further receiving and securely holding a trephine in centered alignment about said defined axis, causes the trephine to move along said defined axis in centered alignment thereabout to precisely cut a specimen of corneal tissue positioned on said cutting block about said defined axis.

2. The corneal press apparatus of claim 1 additionally including a set of modular collets, each of said collets being holdably receivable by said collet-mounting means, each of said collets including trephine-mounting means for receiving and securely holding a trephine of a specifically defined diameter in centered alignment about said defined axis, said set of collets collectively including means for holding trephines of defined diameters over a range of expected diameter cuts.

3. The corneal press apparatus of claim 2 in which said collet mount defines an alignment sight hole therethrough, said alignment sight hole being in alignment with said defined axis, and where said set of collets each define a collet sight hole therethrough which is aligned with said defined axis when said collet is properly mounted onto said collet mount, whereby the alignment with said defined axis of a trephine mounted onto said collet that has, in turn, been mounted onto said collet mount, can be visually inspected by looking through said alignment sight hole and said collet sight hole at a specimen of corneal tissue positioned on said cutting block, and whereby said specimen can be illuminated by directing light through said sight holes.

4. The corneal press apparatus of claim 1 in which said collet mount defines an alignment sight hole therethrough, said alignment sight hole being in alignment with said defined axis, and where said set of collets each define a collet sight hole therethrough which is aligned with said defined axis when said collet is properly mounted onto said collet mount, whereby the alignment with said defined axis of a trephine mounted onto said collet that has, in turn, been mounted onto said collet mount, can be visually inspected by looking through said alignment sight hole and said collet sight hole at a specimen of corneal tissue positioned on said cutting block, and whereby said specimen can be illuminated by directing light through said sight holes.

* * * * *

UNITED STATES PATENT AND TRADEMARK OFFICE
CERTIFICATE OF CORRECTION

PATENT NO. : 5,334,213
DATED : August 2, 1994
INVENTOR(S) : Francis W. Price, Jr., M.D.

It is certified that error appears in the above-identified patent and that said Letters Patent is hereby corrected as shown below:

In column 2, line 49, please change "tile" to --the--.

Signed and Sealed this

Eleventh Day of October, 1994

Attest:

BRUCE LEHMAN

Attesting Officer

Commissioner of Patents and Trademarks